US006218576B1

(12) United States Patent
Shintou et al.

(10) Patent No.: US 6,218,576 B1
(45) Date of Patent: Apr. 17, 2001

(54) PROCESS FOR PRODUCING A DIARYLAMINE

(75) Inventors: Taichi Shintou; Satoru Fujii; Shinji Kubo, all of Kanagawa (JP)

(73) Assignee: Sankio Chemical Co., Ltd., Tokyo (JP)

( * ) Notice: Subject to any disclaimer, the term of this patent is extended or adjusted under 35 U.S.C. 154(b) by 0 days.

(21) Appl. No.: 09/586,752

(22) Filed: Jun. 5, 2000

(30) Foreign Application Priority Data

Jun. 4, 1999 (JP) .................................................. 11-158707

(51) Int. Cl.[7] .................................................. C07C 211/00
(52) U.S. Cl. ............................. 564/435; 564/433; 544/86
(58) Field of Search .................................... 564/433, 435; 544/86

(56) References Cited

U.S. PATENT DOCUMENTS 2,645,662   7/1953   Nimmo et al. ........................ 260/576

FOREIGN PATENT DOCUMENTS 664938    10/1950   (GB) .
6-100504   4/1994   (JP) .............................. C07C/211/54

*Primary Examiner*—Samuel Barts
(74) *Attorney, Agent, or Firm*—Sughrue, Mion, Zinn, Macpeak & Seas, PLLC

(57) ABSTRACT

Described is a process for producing a diarylamine, which comprises subjecting an arylamine to condensation reaction in the co-presence of anhydrous aluminum chloride and anhydrous calcium chloride. The process permits the production of a diarylamine in a high yield at a normal pressure while terminating the reaction in a short time; and also permits the production, at a low cost, of a diarylamine having a high purity to be usable sufficiently as an intermediate for the production of a raw material for an electronic material.

14 Claims, No Drawings

PROCESS FOR PRODUCING A DIARYLAMINE

FIELD OF THE INVENTION

The present invention relates to a process for producing a diarylamine compound, which serves as an important intermediate in the production of organic photoconductors used for electrophotographs, organic electroluminescent devices or the like, dyestuffs, agricultural chemicals, pharmaceuticals and the like, in a high yield, at a high purity and at a low cost.

BACKGROUND OF THE INVENTION

It is the common practice to produce a diarylamine by the Ullmann condensation reaction of an aromatic halide and an arylamine derivative (Chem. Ber., 36, 2382(1902)), Chem. Ber., 40, 4541(1907)) or by subjecting an arylamine to self condensation or subjecting an arylamine and the corresponding arylamine hydrochloride to condensation reaction.

The production by the Ullman reaction is accompanied with the problems that the raw material aromatic halide is expensive and a step for hydrolyzing an amide formed by the condensation reaction is necessary.

In the condensation reaction of an arylamine, on the other hand, it was reported that a diphenylamine was available by heating of aniline and aniline hydrochloride to 300° C. in a solventless manner under a high pressure (Zeitschr. Chem., 438(1866)) and since then, addition of various effective catalysts have been proposed. For example, disclosed are a process of adding anhydrous ferrous chloride (U.S. Pat. No. 2,447,044), a process of adding ammonium chloride (U.S. Pat. No. 2,820,829), a process of adding anhydrous aluminum chloride and ammonium chloride (U.S. Pat. No. 2,645,662), a process of adding anhydrous ferrous chloride and ammonium bromide, and a process of adding cobalt chloride, stannous chloride, cupric chloride, zinc chloride, manganese chloride or the like, and ammonium chloride (U.S. Pat. No. 2,120,966).

In any one of the above-described processes, however, the reaction is conducted under severe conditions of 300 to 400° C. and a high pressure, which requires special equipment such as pressure reactor.

As processes comprising the reaction under a normal pressure, proposed are a process (Zh. Prikl. Khim. (Leningrag). Vol.9, 502(1936)) for synthesizing a diphenylamine by reacting aniline and aniline hydrochloride in the presence of aluminum chloride as a catalyst at 220 to 240° C. for 20 to 25 hours and a process for preparing di-p-tolylamine which comprises reacting p-toluidine in an aromatic solvent in the presence of anhydrous aluminum chloride and ammonium chloride (Unexamined published Japanese patent application No. Hei. 6-100504). These processes, however, need at least 15 hours to complete the reaction and in addition, the diarylamine obtained by each of these processes is not so highly pure as to be usable as an intermediate for the raw material of an electronic material.

SUMMARY OF THE INVENTION

An object of the present invention is to provide a process for producing a diarylamine in a high yield at a low cost which process does not require special equipment such as pressure reactor and can terminate the reaction in a short time even under a normal pressure.

Another object of the present invention is to provide a process for producing, at a low cost, a high-purity diarylamine sufficiently usable as an intermediate for the production of a raw material for an electronic material.

According to the present invention, there is thus provided the below-described process for producing a diarylamine and the object of the present invention is attained by the process.

That is, the present invention provides a process for producing a diarylamine, which comprises subjecting an arylamine to condensation reaction in the presence of anhydrous aluminum chloride and anhydrous calcium chloride.

DETAILED DESCRIPTION OF THE INVENTION

The present invention will hereinafter be described more specifically.

In the present invention, an arylamine as a substrate is preferably represented by the following general formula (I):

$$A\text{—}NH_2 \qquad (I)$$

wherein A represents a substituted or an unsubstituted aryl group.

In formula (I), A is preferably a substituted or an unsubstituted phenyl group, and more preferably a methyl-substituted phenyl group.

In the production process of the present invention, both anhydrous aluminum chloride and anhydrous calcium chloride are used as a catalyst. The reaction in the presence of these catalysts makes it possible to markedly reduce the reaction time and increase the yield, compared with the reaction using a conventionally proposed catalyst. In addition, when these catalysts are employed, a diarylamine having a sufficiently high purity suited for use as an intermediate for the production of a raw material for an electronic material can be obtained by simple purification treatment.

When the reaction is conducted in the presence of one of these catalysts or another combination of catalysts, the reaction time increases and the yield considerably lowers.

Each of anhydrous aluminum chloride and anhydrous calcium chloride is preferably used in a molar ratio (catalyst/arylamine) ranging from 0.05 to 1.0, more preferably from 0.15 to 0.5, still more preferably from 0.20 to 0.35 relative to the arylamine. The molar ratio of anhydrous aluminum chloride to anhydrous calcium chloride (anhydrous aluminum chloride/anhydrous calcium chloride) preferably ranges from 0.2 to 3.0, more preferably from 0.5 to 2.2 and still more preferably from 0.8 to 1.9.

In the production process of the present invention, it is not necessary to use a reaction solvent. As a reaction solvent, however, an aromatic compound having a boiling point of higher than 189° C., preferably 190 to 250° C. or an aliphatic compound having a boiling point of higher than 189° C., preferably 190 to 250° C. is used as needed.

Examples of the aromatic compound having a boiling point of higher than 189° C. include:

(i) aromatic hydrocarbon compounds which may be halogenated, more specifically, diisopropylbenzene, 1-phenylhexane, 1,2-dichlorobenzene, 1,2,4-trichlorobenzene, 1,4-cyclohexylbenzene and diphenylmethane.

(ii) aromatic heterocyclic compounds, more specifically, 2,4-dichloropyrimidine, 2,3,5-trichloropyridine, quinoline, quinazoline and 1,4-benzodioxane.

(iii) aromatic hydrocarbon compounds having a cyclic skeleton which has been partially hydrogenated, for example, dihydrogenated, tetrahydrogenated, hexahydrogenated, octahydrogenated or decahydrogenated, more specifically, 1,4-dihydronaphthalene, 1,2,3,4-tetrahydronaphthalene, 9,10-dihydroanthracene, 9,10-dihydrophenanthrene, 4,5,9,10-tetrahydropyrene, 1,2,3,6,7,8-hexahydropyrene and dodecahydrotriphenylene.

(iv) hydrogenated aromatic heterocyclic compounds, more specifically, 1,2,3,4-tetrahydroquinoline, 5,6,7,8-tetrahydroquinoline, 1,2,3,4-tetrahydroisoquinoline, 5,6,7,8-tetrahydroisoquinoline, 1-phenylpiperidine, 1-phenylpiperazine, indoline and julolidine.

Examples of the aliphatic compound having a boiling point of higher than 189° C. include:

(v) saturated aliphatic compounds, more specifically, undecane, dodecane, tridecane, 2-methyldodecane, 4-ethylundecane, tetradecane, pentadecane, 3,3-dimethyltridecane, hexadecane, heptadecane, 2-methyl-4-ethyltetradecane.

(vi) unsaturated aliphatic compounds, more specifically, 1-undecene, 4-dodecene, 3,3-dimethyl-l-decene, 1,3,5-dodecatriene, 5-tridecene, 3-methyl-4-ethyl-2-decene, 1-dodecyne, 3-dodecen-1-yne, 1-tridecine, 5,5-dimethyl-3-undecen-1-yne and 5-ethynyl-1,3-dodecadiene.

(vii) saturated alicyclic compounds, more specifically, dicyclohexane, decahydronaphthalene and dodecahydrofluorene.

(viii) unsaturated alicyclic compounds, more specifically, cyclododecene, 1,5,9-cyclodecatriene, (−)-β-bisabolene, α-humulene, α-camphorene, cembrene, (−)-β-cadinene, (−)-β-caryophyllene, (−)-β-santalene, (−)-(α-cedrene and (+)-β-selinene.

(ix) saturated aliphatic heterocyclic compounds, more specifically, 1,4,7-trithiacyclononane, 1,4,7-trithiacyclodecane, 1,4,7,10-tetraoxacyclododecane, 1,4,7,10,13-pentaoxacyclopentadecane, 1,4,7-triazacyclononane, 1,4,7,10-tetraazacyclododecane.

(x) unsaturated aliphatic heterocyclic compounds, more specifically, 1,4,5,6-tetrahydropyrimidine and 1-pyrrolidinβ-1-cyclohexane.

These aromatic compounds and aliphatic compounds may be used either singly or in combination as the solvent.

Among the above-exemplified compounds, partially hydrogenated aromatic hydrocarbons, saturated aliphatic compounds and saturated alicyclic compounds are preferred, and particularly 1,2,3,4-tetrahydronaphthalene, decahydronaphthalene, undecane, dodecane, tridecane and tetradecane are preferably used. By the use of such a preferred solvent, the reaction can be terminated in a short time and the target compound can be obtained in a high yield. A particularly preferred solvent is 1,2,3,4-tetrahydronaphthalene, because when it is used, a substance sublimed from the reaction system does not adhere to a reactor.

The above-described reaction solvent having a boiling point of at least 190° C. is generally used in an amount ranging from 20 to 300 ml, preferably 50 to 150 ml, relative to 1 mol of an arylamine.

The reaction proceeds under a normal pressure so that special equipment such as pressure reactor resistant to a high pressure is not always necessary.

The reaction is usually conducted at 190° C. or greater, preferably 190 to 250° C., at a normal pressure. The reaction time may usually range from 3 to 6 hours and the reaction is completed in a short time.

After completion of the reaction, a high-purity diarylamine can be obtained by the simple purification method as described below, but the method is not limited thereto.

Described specifically, after completion of the reaction, the reaction mixture is cooled. A non-water-soluble organic solvent such as toluene or ethyl acetate is added thereto in an amount of about 50 to 500 parts by weight relative to 100 parts by weight of an arylamine, the raw material. The resulting mixture is charged in ice water, followed by stirring. The reaction mixture is allowed to stand, whereby it is separated into an organic layer and a water layer. In the water layer, inorganic substances such as the residue of the catalysts have been extracted so that it is removed. The organic layer containing the diarylamine is obtained by separation, followed by distillation or concentration of the organic layer under reduced pressure to remove the organic solvent. An alcohol such as methanol or isopropyl alcohol is added to the residue to crystallize it, whereby the corresponding high-purity diarylamine can be obtained.

As the diarylamine compound to be produced by the process of the present invention, diarylamine compounds represented by the below-described formula (II) can be mentioned as an example.

$$A1—NH—A2 \quad\quad\quad (II)$$

wherein A1 and A2, which may be the same or different, each represents a substituted or an unsubstituted aryl group.

A1 and A2 each preferably represents an aryl group having a binding hand at any position of the aromatic ring of each of the compounds represented by the following formulas, but is not limited thereto.

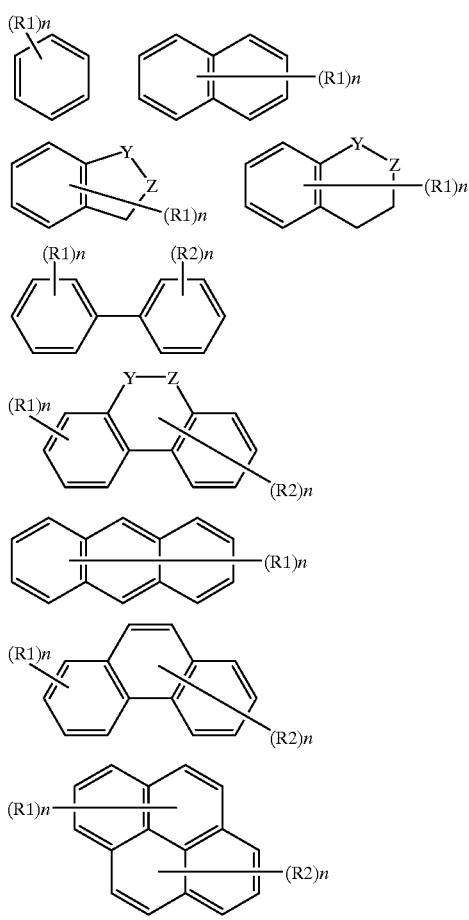

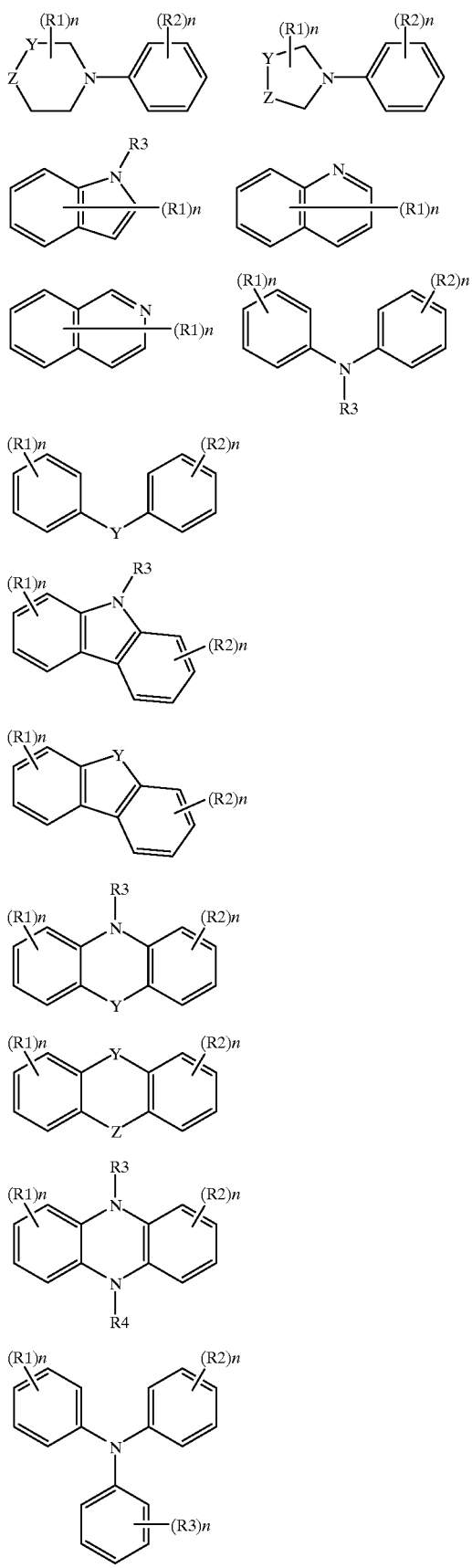

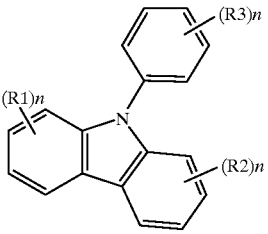

In the above-described formulas, Y and Z are the same or different and each independently represents an atom or group selected from —CH=, —CH$_2$—, oxygen atom, sulfur atom or —N(R3)—.

R1 to R4 each represents a substituent having a Hammett's substituent constant am of −0.21 to 0.39 and it may bond to any position of the aromatic ring. When n stands for an integer of 2 to 5, they may be the same or different in the same ring. When R3 or R4 bonds directly to a nitrogen atom, R3 or R4 represents a hydrogen atom or a group bonding to the nitrogen atom through a carbon atom.

n represents an integer of 0 to 5.

Specific examples of the substituent having a Hammett's substituent constant am ranging from −0.21 to 0.39 include alkyl, cycloalkyl, aryl, alkoxy, phenoxy and dialkylamino groups and halogen atoms.

As the diarylamine compound represented by the formula (II), the following ones can be mentioned as examples.

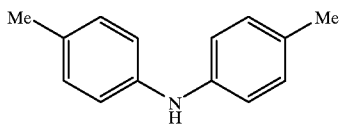
(I-1)

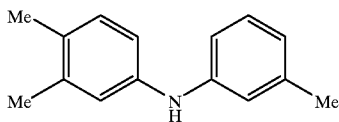
(I-2)

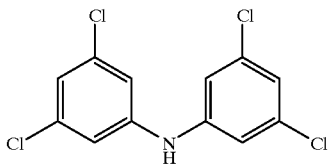
(I-3)

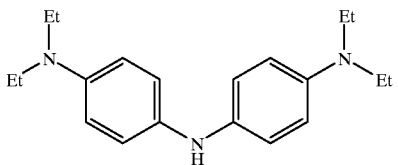
(I-4)

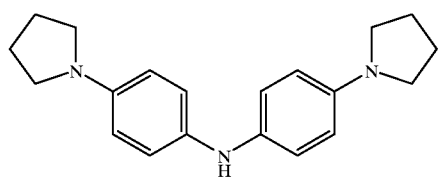
(I-5)

EXAMPLES

The present invention will hereinafter be described by examples in further detail. It should however be borne in mind that the present invention is not limited thereto. The purity was evaluated by high-performance liquid chromatography (which will hereinafter be abbreviated as "HPLC").

Example 1

Synthesis of bis(4-methylphenyl)amine (I-1)

In a 500-ml four-necked flask were charged 56 ml of 1,2,3,4-tetrahydronaphthalene (boiling point: 207° C.) as a solvent and 91.1 g (0.83 mol) of p-toluidine, followed by the addition of 25.6 g (0.23 mol) of anhydrous calcium chloride and 30.8 g (0.23 mol) of anhydrous aluminum chloride under stirring. The resulting mixture was reacted at 210 to 220° C. for 3 hours under a nitrogen atmosphere. After cooling, the reaction mixture was added with 126 ml of toluene, followed by charging in 160 g of ice water. The resulting mixture was stirred and allowed to stand, and then the resulting water layer was separate out. The organic layer was washed successively with 150 ml of a 5% aqueous solution of hydrochloric acid, 100 ml of a 5% aqueous solution of sodium bicarbonate and 100 ml of water. After removal of the organic solvent by distillation under reduced pressure, 80 ml of methanol was added to the residue and the mixture was crystallized overnight at −3 to −8° C. The resulting crystals were collected by filtration, washed with 30 ml of methanol and then dried, whereby 57.1 g (yield: 69.8%) of the title compound was obtained as white crystals. As a result of HPLC. analysis (column: YMC-A-312, detection UV: 280 nm, flow rate: 1.0 ml/min, eluent: acetonitrile/water=8/2), the compound was found to have a purity of 99.8%.

Example 2

Synthesis of 3,4-dimethylphenyl-3-methylphenylamine (I-2)

In a 500-ml four-necked flask were charged 56 ml of 1,2,3,4-tetrahydronaphthalene (boiling point: 207° C.) as a solvent and 45.0 g (0.42 mol) of m-toluidine, followed by the addition of 25.6 g (0.23 mol) of anhydrous calcium chloride and 30.8 g (0.23 mol) of anhydrous aluminum chloride under stirring. After stirring at an internal temperature of 100 to 120° C. for 30 minutes under a nitrogen atmosphere, the reaction mixture was added with 50.9 g (0.42 mol) of 3,4-xylidine. The resulting mixture was reacted at an internal temperature of 210 to 220° C. for 3 hours. After cooling, the reaction mixture was added with 126 ml of toluene, followed by charging in 160 g of ice water. The resulting mixture was stirred and then, allowed to stand, whereby a water layer was separated out. The organic layer was washed successively with 150 ml of a 5% aqueous solution of hydrochloric acid, 100 ml of a 5% aqueous solution of sodium bicarbonate and 100 ml of water. From the organic solvent, the distillate at 134 to 135° C. and a vacuum degree of 0.4 to 0.5 Torr was collected, whereby 37.9 g (yield: 42.7%) of the title compound was obtained as a slightly yellow oil. As a result of HPLC. analysis (column: YMC-A-312, detection UV: 280 nm, flow rate: 1.0 ml/min, eluent: acetonitrile/water=8/2), the compound was found to have a purity of 99.3%.

Example 3

Synthesis of bis(4-morpholinophenyl)amine (1-6)

In a 300-ml four-necked flask were charged 68 ml of decahydronaphthalene (boiling point: 190° C.) as a solvent and 17.8 g (0.50 mol) of 4-morpholinoaniline, followed by the addition of 15.4 g (0.138 mol) of anhydrous calcium chloride and 18.5 g (0.138 mol) of anhydrous aluminum chloride under stirring. The resulting mixture was reacted at 200 to 210° C. for 5 hours under a nitrogen atmosphere. After cooling, the reaction mixture was added with 76 ml of toluene, followed by charging in 96 g of ice water. The resulting mixture was stirred and allowed to stand, and then, the resulting water layer was separated out. The organic layer was washed successively with 90 ml of a 5% aqueous solution of hydrochloric acid, 60 ml of a 5% aqueous solution of sodium bicarbonate and 60 ml of water. After removal of the organic solvent by distillation under reduced pressure, 48 ml of isopropyl alcohol was added to the residue and the mixture was crystallized overnight at −3 to −8° C. The resulting crystals were collected by filtration, washed with 18 ml of isopropyl alcohol and then dried, whereby 44.9 g (yield: 58.4%) of the title compound was obtained as white crystals. As a result of HPLC. analysis (column: YMC-A-312, detection UV: 280 nm, flow rate: 1.0 ml/min, eluent: acetonitrile/water 7/3), the compound was found to have a purity of 99.7%.

Example 4

Synthesis of bis(4-diphenylaminophenyl)amine (I-17)

In a 500-ml four-necked flask were charged 68 ml of tridecane (boiling point: 234° C.) as a solvent and 130.2 g (0.50 mol) of 4-diphenylaminoaniline, followed by the addition of 15.4 g (0.138 mol) of anhydrous calcium chloride and 18.5 g (0.138 mol) of anhydrous aluminum chloride under stirring. The resulting mixture was reacted at 210 to 220° C. for 3 hours under a nitrogen atmosphere. After cooling, the reaction mixture was added with 114 ml of toluene, followed by charging in 144 g of ice water. The resulting mixture was stirred and allowed to stand, and then the resulting water layer was separated out. The organic layer was washed successively with 90 ml of a 5% aqueous solution of hydrochloric acid, 60 ml of a 5% aqueous solution of sodium bicarbonate and 60 ml of water. After removal of the organic solvent by distillation under reduced pressure, 72 ml of isopropyl alcohol was added to the residue and the mixture was crystallized overnight at −3 to −8C. The resulting crude crystals were collected by filtration, washed with 27 ml of isopropyl alcohol and then dried, whereby 84.2 g (yield: 66.9%) of the title compound was obtained as pale yellow crystals. As a result of HPLC. analysis (column: YMC-A-312, detection UV: 280 nm, flow rate: 1.0 ml/min, eluent: methanol/tetrahydrofuran=99/1), the compound was found to have a purity of 99.7%.

From the results of Examples 1 to 4, it is apparent that the process of the present invention makes it possible to complete the reaction in a short time, to produce a diarylamine compound in a high yield and in addition, to produce a markedly high-purity diarylamine compound by simple purification treatment.

Comparative Examples 1 to 8

In each of Comparative Examples 1 to 8, anhydrous aluminum chloride and anhydrous calcium chloride used as the catalysts in Example 1 were replaced by the catalyst shown in Table 1, and the reaction time was also changed to that shown in Table 1, whereby bis(4-methylphenyl)amine was synthesized. In other words, in a similar manner to Example 1 except that the kind of the catalyst and reaction time were changed, yield and HPLC purity of each of the resulting compounds were evaluated. Results of the comparative examples, as well as the results of Example 1 are shown in Table 1.

TABLE 1

| | Catalyst | Reaction time (hr) | Yield (%) | Purity (%) as measured by HPLC |
|---|---|---|---|---|
| Example 1 | $AlCl_3/CaCl_2$ | 3.0 | 69.8 | 99.8 |
| Comp. Ex. 1 | $AlCl_3$ | 7.0 | 33.9 | 98.2 |
| Comp. Ex. 2 | $AlCl_3/NH_4Cl$ | 6.0 | 50.0 | 98.0 |
| Comp. Ex. 3 | $AlCl_3/NH_4Br$ | 7.0 | 41.9 | 98.0 |
| Comp. Ex. 4 | $AlCl_3/NaCl$ | 5.0 | 52.3 | 98.5 |
| Comp. Ex. 5 | $AlCl_3/KCl$ | 6.0 | 45.8 | 98.2 |
| Comp. Ex. 6 | $AlCl_3/CuCl$ | 8.0 | 33.2 | 98.0 |
| Comp. Ex. 7 | $AlCl_3/SnCl_2$ | 12.0 | 15.9 | 96.5 |
| Comp. Ex. 8 | $AlCl_3/FeCl_2$ | 15.0 | 12.0 | 96.2 |

From the results shown in Table 1, it is apparent that the reaction is completed in a shorter time and the yield is better in Example 1 wherein an arylamine is subjected to condensation reaction in the co-presence of aluminum chloride and calcium chloride as catalysts, compared with Comparative Examples 1 to 8 wherein a single catalyst or combination with another catalyst is employed; and in Example 1, a remarkably high-purity diarylamine compound can be obtained by simple purification treatment.

The production process according to the present invention makes it possible to complete the reaction in a short time without using special equipment such as pressure reactor, since the reaction proceeds at a normal pressure and therefore reaction under a high pressure is not necessary; and to produce a diarylamine in a high yield at a low cost. The diarylamine produced by the production process of the present invention can be obtained as that having a high purity by a simple purification step so that it can be used sufficiently as an intermediate for the production of a raw material for an electronic material.

While the invention has been described in detail and with reference to specific embodiments thereof, it will be apparent to one skilled in the art that various changes and modifications can be made therein without departing from the spirit and scope thereof.

This application is based on Japanese patent application Hei-11-158707, filed on Jun. 4, 1999, incorporated herein by reference.

What is claimed is:

1. A process for producing a diarylamine, which comprises subjecting an arylamine to condensation reaction in the presence of anhydrous aluminum chloride and anhydrous calcium chloride.

2. The process for producing a diarylamine as in claim 1, wherein the arylamine is represented by the following general formula (I):

$$A—NH_2 \qquad (I)$$

wherein A represents a substituted or an unsubstituted aryl group.

3. The process for producing a diarylamine as in claim 2, wherein A is a substituted or an unsubstituted phenyl group.

4. The process for producing a diarylamine as in claim 2, wherein A is a methyl-substituted phenyl group.

5. The process for producing a diarylamine as in claim 1, wherein the amount of each of anhydrous aluminum chloride and anhydrous calcium chloride is 0.05 to 1.0 mol per mol of the arylamine.

6. The process for producing a diarylamine as in claim 1, wherein the amount of each of anhydrous aluminum chloride and anhydrous calcium chloride is 0.20 to 0.35 mol per mol of the arylamine.

7. The process for producing a diarylamine as in claim 1, wherein the molar ratio of anhydrous aluminum chloride to anhydrous calcium chloride is from 0.2 to 3.0.

8. The process for producing a diarylamine as in claim 1, wherein the molar ratio of anhydrous aluminum chloride to anhydrous calcium chloride is from 0.5 to 2.2.

9. The process for producing a diarylamine as in claim 1, wherein the molar ratio of anhydrous aluminum chloride to anhydrous calcium chloride from 0.8 to 1.9.

10. The process for producing a diarylamine as in claim 1, wherein the reaction is carried out by using a reaction solvent having a boiling point of higher than 189° C.

11. The process for producing a diarylamine as in claim 10, wherein the reaction solvent is a partially hydrogenated aromatic hydrocarbon.

12. The process for producing a diarylamine as in claim 10, wherein the reaction solvent is a saturated aliphatic compound.

13. The process for producing a diarylamine as in claim 10, wherein the reaction solvent is a saturated alicyclic compound.

14. The process for producing a diarylamine as in claim 10, wherein the reaction solvent is selected from the group consisting of 1,2,3,4-tetrahydronaphthalene, decahydronaphthalene, undecane, dodecane, tridecane and tetradecane.

* * * * *